United States Patent [19]

Sprecker et al.

[11] 4,264,456

[45] Apr. 28, 1981

[54] BENZODIOXANONES AND ORGANOLEPTIC USES THEREOF

[75] Inventors: Mark A. Sprecker, Sea Bright; John B. Hall, Rumson; Frederick L. Schmitt, Holmdel, all of N.J.

[73] Assignee: International Flavors & Fragrances Inc., New York, N.Y.

[21] Appl. No.: 145,984

[22] Filed: May 2, 1980

Related U.S. Application Data

[62] Division of Ser. No. 75,071, Sep. 13, 1979.

[51] Int. Cl.³ .................................... A23L 1/226
[52] U.S. Cl. .................................... 252/8.9; 8/137; 252/8.6; 252/174.11; 260/340.2
[58] Field of Search .................... 252/8.9, 8.6

[56] References Cited

U.S. PATENT DOCUMENTS

| | | | |
|---|---|---|---|
| 2,540,988 | 2/1951 | Mowry | 260/340.2 |
| 3,647,479 | 3/1972 | Beereboom et al. | 426/536 |
| 3,952,016 | 4/1976 | Barillo et al. | 568/680 |
| 3,959,185 | 5/1976 | Barillo et al. | 424/70 |
| 4,010,207 | 3/1977 | Hall et al. | 568/433 |

Primary Examiner—A. Lionel Clingman
Attorney, Agent, or Firm—Liberman, Arthur L.

[57] ABSTRACT

Described are the bicyclic compounds having the generic structure:

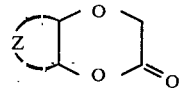

wherein Z is benzo or cyclohexano and processes for preparing same and compositions containing same for use in augmenting or enhancing the aroma and/or taste of foodstuffs, chewing gums, toothpastes and medicinal products; tobacco; perfumes, colognes and perfumed articles, produced by a process described by the reaction:

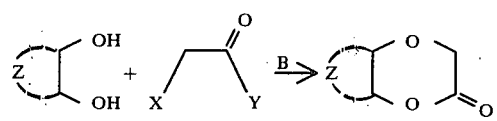

wherein X is chloro or bromo; Y is chloro, bromo or OR; R is $C_1$–$C_3$ lower alkyl, that is: methyl, ethyl, n-propyl or i-propyl; B is MOH, MH, MOR', trialkylamine, or $M_2$–$CO_3$ (wherein M is alkali metal such as sodium or potassium); and R' is $C_1$–$C_5$ lower alkyl, such as methyl, ethyl, n-propyl, i-propyl and t-butyl with the proviso that B is trialkylamine or an alkali metal carbonate when Y is chloro or bromo and B is MOH, MH or MOR' when Y is OR.

The above mentioned compounds produce:
A. In foodstuffs, chewing gums and medicinal products, a sweet, green, fruity, coumarinic, marzipan-like aroma and taste.
B. In tobacco, a sweet, spicy, vanilla-like, woody, hay, tobacco-like aroma prior to smoking and a sweet, spicy, hay, tobacco-like aroma on smoking.
C. In perfumes, colognes and perfumed articles, sweet, fruity, and green aroma nuances.

2 Claims, 4 Drawing Figures

NMR SPECTRUM FOR EXAMPLE I.

IR SPECTRUM FOR EXAMPLE I.

NMR SPECTRUM FOR EXAMPLE III.

IR SPECTRUM FOR EXAMPLE III.

BENZODIOXANONES AND ORGANOLEPTIC USES THEREOF

This is a divisional of application Ser. No. 075,071, filed Sept. 13, 1979 allowed.

BACKGROUND OF THE INVENTION

The present invention relates to bicyclic compounds having the generic structure:

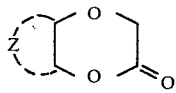

wherein Z is cyclohexano or benzo and novel compositions using such cyclic compounds to augment or enhance the flavor and/or aroma of consumable materials.

There has been considerable work performed relating to substances which can be used to impart (augment or enhance) flavors and fragrances to (or in) various consumable materials. These substances are used to diminish the use of natural materials some of which may be in short supply and to provide more uniform properties in the finished product.

Sweet, green, fruity, coumarinic, marzipan-like aromas and tastes are particularly desirable for many uses in foodstuff, chewing gum, toothpaste and medicinal product flavors. Sweet, spicy, vanilla-like, woody, hay, tobacco-like aromas prior to smoking and sweet, spicy, hay, tobacco-like aromas on smoking are desirable in tobacco and tobacco flavor compositions especially where these notes appear both in the mainstream and the sidestream on smoking as well as prior to smoking. Sweet, fruity, and green aroma nuances are especially desirable in several types of perfume compositions, perfumed articles e.g., anionic, cationic and nonionic solid or liquid detergents and colognes.

The foregoing organoleptic properties have heretofore been provided by coumarin or homologues or analogs thereof having the structures:

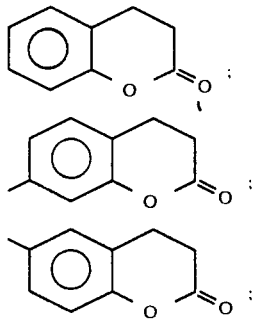

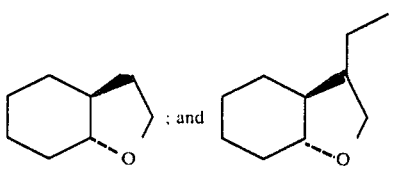

Coumarin, 1,2-benzopyrone having the structure:

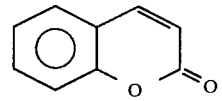

is described in "Perfume and Flavor Chemicals (Aroma Chemicals)" by Stephen Arctander, 1969 (Monograph 704) as being extensively used in perfumery to support herbaceous odors, lavender, lavandin, rosemary, citrus oils, oakmoss etc., and as a fixative in numerous types of fragrances. Arctander states that coumarin is almost a standard ingredient in Fougère types with amyl salicylate and lavender notes with or without Oakmoss. Arctander states that coumarin is not permitted for food use in the United States of America and is also banned from food flavorings in a number of other countries. Arctander further states that the hazardous level of coumarin is estimated at 3 grams per day for adult human beings. Accordingly, it has been found necessary in the flavor and fragrance industry to find a suitable replacement for coumarin.

Thus, the compounds of the instant case having the generic structure:

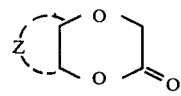

wherein Z is benzo or cyclohexano which generic structure includes the structures:

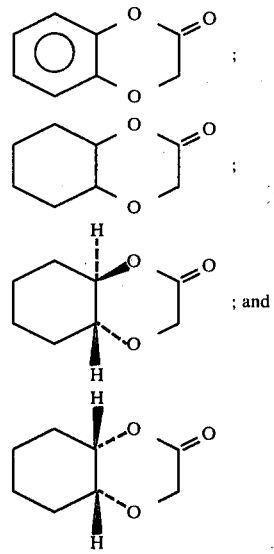

were designed as analogs for 6-methyl coumarin, 7-methyl coumarin and coumarin itself, having the structures:

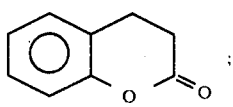

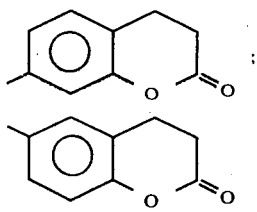

However, these coumarin derivatives have been indicated to have displayed photosensitization in toxicological testing and it is therefore been ascertained to be prudent to replace same.

Other known coumarin analogs do exist having the structures:

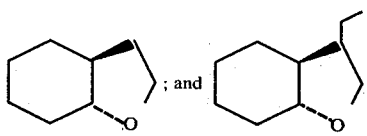

however, these analogs are so expensive that it is not possible to produce them as replacements for coumarin.

The compound having the generic structure:

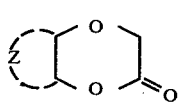

is an inexpensive replacement which is produced using readily available starting materials.

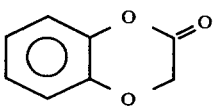

Figure 2:
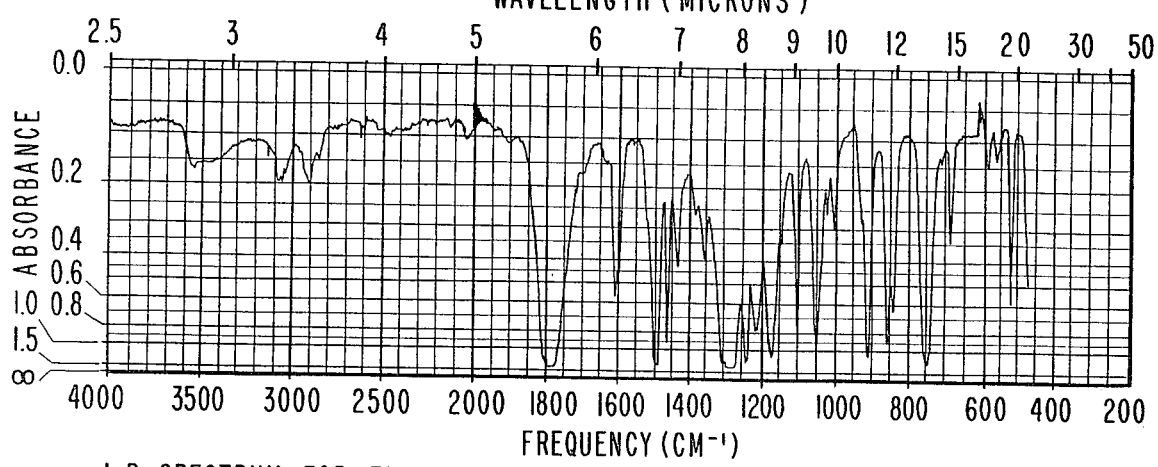

FIG. 2 is the infrared spectrum for the compound produced according to Example I having the structure:

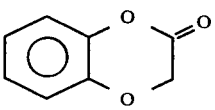

Figure 3:
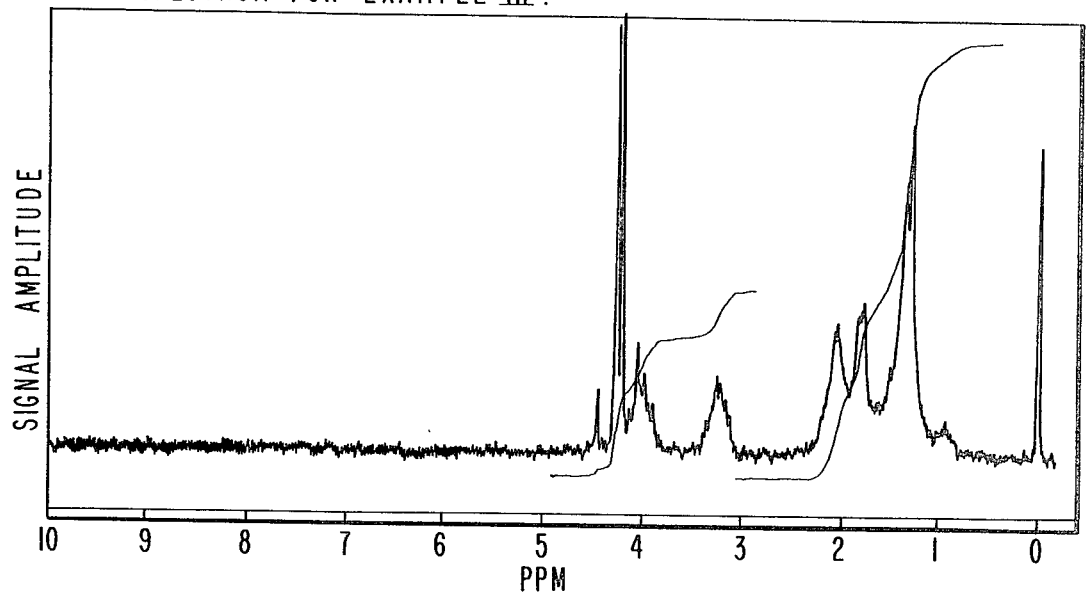

FIG. 3 is the NMR spectrum for the compound produced according to Example III having the structure:

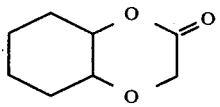

Figure 4:
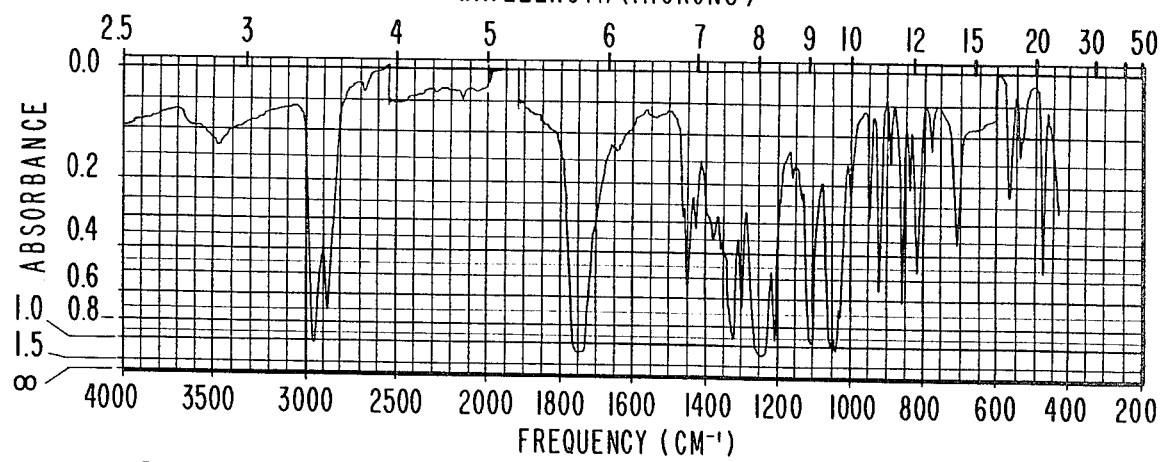

FIG. 4 is the infrared spectrum for the compound prepared according to the process of Example III having the structure:

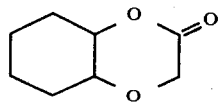

THE INVENTION

It has now been discovered that novel solid and liquid foodstuff, chewing gum, toothpaste and medicinal products and flavoring compositions having a sweet, green, fruity, coumarinic, marzipan-like aroma and taste characteristics; novel perfume compositions, perfumed articles (such as anionic, cationic, and nonionic solid and liquid detergents, disposable fabric softener articles and cosmetic powders) and colognes having sweet, fruity, and green aroma nuances, as well as novel smoking tobaccos and smoking tobacco flavoring compositions having sweet, spicy, vanilla-like, woody, hay, tobacco-like aromas prior to smoking and sweet, spicy, hay, tobacco-like aromas on smoking may be provided by the utilization of bicyclic compounds having the structure:

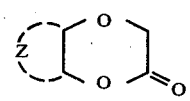

wherein Z is benzo or cyclohexano.

The generic structure:

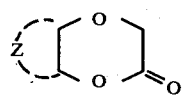

is intened herein to cover compounds having the structure:

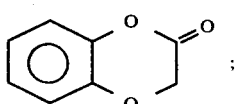

;

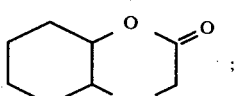

;

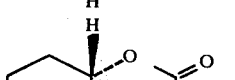

; and

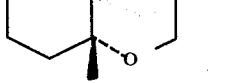

wherein the structures:

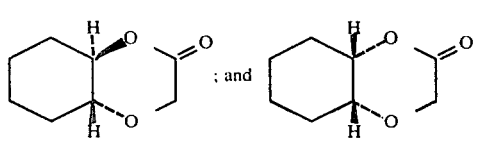

are, respectively, the "trans" and "cis" isomers of the compound having the generic structure:

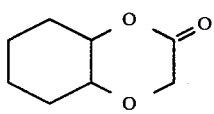

Because of their organoleptic properties and their low cost of manufacture as well as their excellent toxicological properties the compounds defined according to the structure:

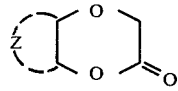

have unique, unexpected and advantageous properties over coumarin and its analogs and homologues having the structures:

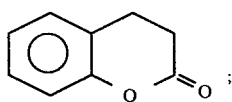

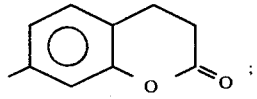

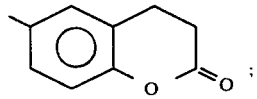

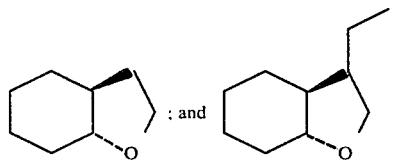

The compounds having the structure defined according to the genus:

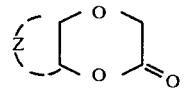

wherein Z is benzo or cyclohexano useful as indicated, supra, may be produced by processes defined according to the reaction scheme:

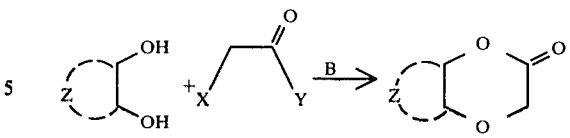

wherein X is chloro or bromo; Y is chloro, bromo or —OR; with R being $C_1$-$C_3$ lower alkyl such as methyl, ethyl, n-propyl or i-propyl; where B is MOH; MH; MOR'; a trialkylamine or $M_2$—$CO_3$ with M being an alkali metal such as sodium or potassium and R' being $C_1$-$C_5$ alkyl such as methyl, ethyl, i-propyl, n-propyl or t-butyl with the proviso that B is trialkylamine or $M_2$—$CO_3$ when Y is Cl or Br and B is MOH, MH, or MOR' when Y is —OR. The foregoing generic reaction scheme is exemplified by the following three specific reaction schemes:

Reaction Scheme I

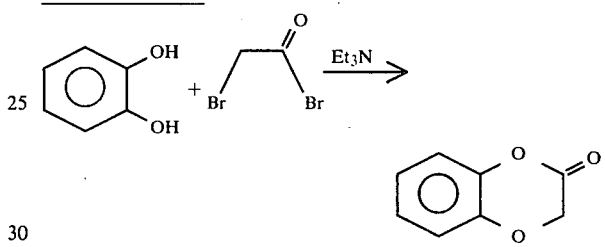

Reaction Scheme II

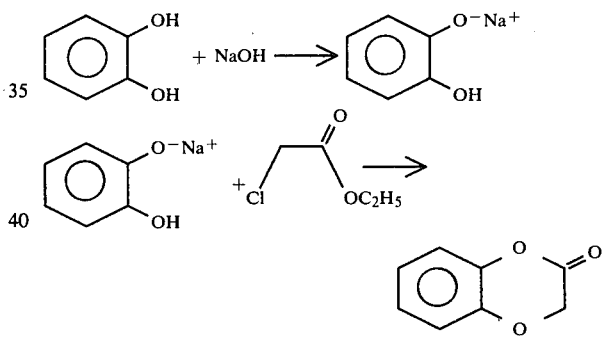

Reaction Scheme III

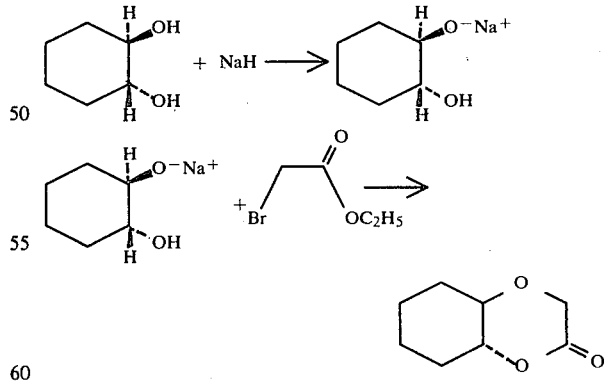

Concerning the reaction Scheme I, to wit:

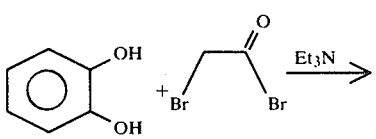

-continued

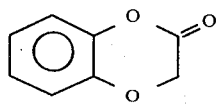

it is preferred to use chloroacetyl chloride or bromoacetyl bromide in the presence of a non-nucleophilic base such as a tertiary amine such as triethylamine or an alkali metal carbonate such as sodium carbonate. It is preferred that the mole ratio of haloacetylhalide:base be about 1:2 and that the mole ration of catechol:-haloacetylhalide be about 1:1. The reaction should be carried out in a solvent such as tetrahydrofuran, toluene, diethylether or chloroform each of which is inert to the reaction mass. The reaction temperature may vary from about 40° C. up to the reflux temperature of the solvent at the pressure at which the reaction is carried out. The pressure that the reaction may be carried out may vary from 0.5 atmospheres up to 20 atmospheres with a pressure of 1 atmosphere being preferred. Thus, higher pressures do not give rise to any increase in yield and give rise to a more expensive process in view of the more expensive equipment that must be utilized.

Insofar as Reaction Scheme II, to wit, involving the two reactions:

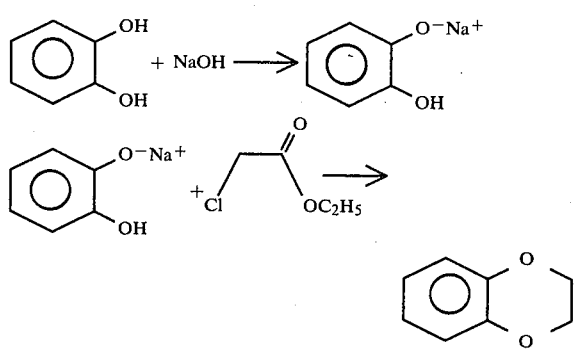

it is preferred that the phase transfer agent be used along with the base which may be any alkali metal hydroxide, e.g. LiOH, NaOH or KOH. The phase transfer agent may be any of those described in U.S. Pat. No. 4,010,207, issued on Mar. 1, 1977, for example, Aliquat ® 336 (a brand of tricapryl methyl ammonium chloride produced by the General Mills Chemical Company of Minneapolis, Minn.). It is preferred that the alkylhaloacetate used be either ethyl chloroacetate or ethyl bromoacetate. It is preferred that the concentration of phase transfer agent be from 5 up to 20 grams of phase transfer agent per mole of alkali metal hydroxide. Furthermore, it is preferred that an inert solvent be used in the reaction such as toluene or chloroform.

Insofar as Reaction Scheme III is concerned, that is wherein the reaction examplified by the following sequence is carried out:

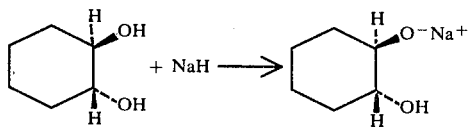

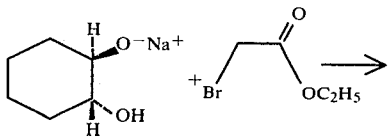

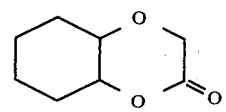

the NaH may be replaced by an alkali metal hydride such as KH or LiH as well as an alkali metal alkoxide such as sodium methylate or an alkali metal butoxide such as potassium t-butoxide. Insofar as the first step of the reaction is concerned, the reaction is carried out using an inert solvent such as tetrahydrofuran, xylene, benzene or diethylether. Insofar as the second part of this reaction sequence is concerned, it is preferred that the mole ratio of catechol salt:alkylhaloacetate be about 1:1 and it is preferred that the reaction be carried out in an inert solvent such as toluene, benzene, xylene, chloroform or diethylether at a temperature of from about 40° C. up to about reflux; preferably at a temperature of about 80° C.

The compound having the generic structure:

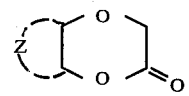

hereinafter referred to as the "cyclic chemical compounds" of our invention are capable of supplying and/or potentiating certain flavor and aroma notes usually lacking in many fruit flavors as well as tobacco flavors heretofore. Furthermore, the cyclic chemical compounds of our invention are capable of supplying certain fragrance notes usually lacking in many perfumery materials, for example, Fougère formulations, lavendin formulations, citrusy formulations, and oakmoss type formulations. In addition these materials are capable of acting as fixatives in perfumery while augmenting or enhancing certain aroma nuances in themselves.

When the cyclic chemical compounds of our invention are used as foodstuff flavor adjuvants the nature of the co-ingredients included with said cyclic chemical compounds in formulating the product composition will also serve to alter, augment or enhance the organoleptic characteristics of the ultimate foodstuff treated therewith.

As used herein, the term "foodstuff" includes both solid and liquid ingestible materials which usually do, but need not, have nutritional value. Thus, foodstuffs includes soaps, convenience foods, beverages, dairy products, candies, vegetables, cereals, soft drinks, snacks and the like.

As used herein, the term "medicinal products" includes both solids and liquids which are ingestible non-toxic materials which have medicinal value such as cough syrups, cough drops, and chewable medicinal tablets.

The term "chewing gum" is intended herein to be a foodstuff composition comprising a substantially water-insoluble, chewable plastic gum base such as chicle, or substitutes therefor, including jelutong, guttakay rubber or certain comestible natural or synthetic resins or waxes. Incorporated with the gum base in admixture therewith may be plasticizers or softening agents, e.g., glycerine; and a flavoring composition which incorporates one or more of the cyclic chemical compounds of our invention, and, in addition, sweetening agents which may be sugars, including sucrose or dextrose and/or artificial sweeteners such as cyclamates or saccharin. Other optional ingredients may be present.

The term "augment" in its various forms is used herein to mean the supplying, modifying or imparting of a flavor or aroma characteristic, note or nuance to an otherwise bland, relatively tasteless or non-odorous substance or modifying an existing flavor or aroma characteristic where the natural flavor is deficient in some regard, or supplementing the existing flavor or aroma impression to modify its quality, character, taste or aroma.

The term "enhance" is used herein to mean the intensification of a flavor or aroma characteristic or note without the modification of the quality thereof. Thus, "enhancement" of a flavor or aroma means that the enhancement agent does not add any additional flavor note or nuance.

Substances suitable for use herein as co-ingredients or flavoring adjuvants are well known in the art for such use, being extensively described in the relevant literature. It is required that any such material be "ingestibly acceptable", and thus non-toxic or otherwise non-deleterious, particularly from an organoleptic standpoint whereby the ultimate flavor and/or aroma of the consumable material used does not cause the consumable material to have unacceptable aroma and taste nuances.

It is a further requirement that such material be organoleptically compatible with the foodstuff with which it is used so that the flavor and aroma nuances of such material, taken together with the flavor and aroma nuances of the foodstuff (as a whole) give rise to a harmoniously aesthetically pleasing aroma and taste profile. Such material, in general, may be characterized as flavoring adjuvants or vehicles comprising broadly, stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates; starches, pectins, and emulsifiers, e.g., mono- and diglycerides of fatty acids, skim milk powder, hexoses, pentoses, disaccharides, e.g., sucrose corn syrup and the like.

Surface acive agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcumin and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobuyric acid, isovaleric acid, alpha-methyl-butyric acid, propionic acid, valeric acid, 2-methyl-2-pentenoic acid, and 2-methyl-cis-3-pentenoic acid; ketones and aldehydes, e.g., acetaldehyde, acetophenone, acetone, acetyl methyl carbinol, acrolein, n-butanal, crotonal, diacetyl, beta,beta-dimethylacrolein, n-hexanal, 2-hexenal, cis-3-hexenal, 2-heptenal, 4-(p-hydroxyphenyl)-2-butanone, alpha-ionone, beta-ionone, 2-methyl-3-butanone, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpienol, cis-terpineol hydrate; esters, such as butyl acetate, ethyl acetate, ethyl acetoacetate, ethyl benzoate, ethyl butyrate, ethyl caprocate, ethyl cinnamate, ehyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, methyl-2-methylbutyrate, propyl acetate, amyl acetae, amyl butyrate, benzyl salicylate, dimethyl anthranilate, ethyl methylphenylglycidate, ethyl succinate, isobutyl cinnamate and terpenyl acetate; essential oils, such as jasmine absolute, rose absolute, orris absolute, lemon essential oil, Bulgarian rose, yara yara, natural raspberry oil and vanilla, lactones, sulfides, e.g., methyl sulfide and other materials such as maltol, acetoin and acetals (e.g., 1,1-diethoxyethane,1,1-dimethoxyethane and dimethoxymethane.

The specific flavoring adjuvant selected for use may be either solid or liquid depending upon the desired physical form of the ultimate product, i.e., foodstuff, whether simulated or natural, and should, in any event, be capable of providing an environment in which the cyclic chemical compounds can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of cyclic chemical compound(s) employed in a particular instance can vary over a relatively wide range whereby its desired organoleptic effects (having reference to the nature of the product) are achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected, (to be effective) be sufficient to augment or enhance the organoleptic characteristics of the parent composition, (whether foodstuff per se or flavoring composition).

The use of insufficient quantities of cyclic chemical compounds will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of cyclic chemical compounds ranging from a small but effective amount, e.g., 0.5 parts per million up to about 20 parts per million by weight based on total composition are suitable. Concentrations in excess of the maximum quantity stated are not thermally recommended, since they fail to prove commensurate enhancement of organoleptic properties. In those instances, wherein the cyclic chemical compounds are added to the foodstuff as an integral component of a flavoring composition, it is, of course, essential that the total quantity of flavoring composition employed be sufficient to yield an effective cyclic chemical compound concentration in the foodstuff product.

Food flavoring compositions prepared in accordance with the present invention preferably contain the cyclic chemical compound in concentrations ranging from about 0.1% up to about 15% by weight based on the total weight of said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing one or more of the cyclic chemical compounds of our invention with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powdered mix are obtained by mixing the dried solid components, e.g., starch, sugar and the like and cyclic chemical compounds in a dry blender until the requisite degree of uniformity is achieved.

It is presently preferred to combine with the cyclic chemical compounds the following adjuvants:
p-Hydroxybenzyl acetone;
Geraniol;
Acetaldehyde;
Maltol;
Ethyl methyl phenyl glycidate;
Benzyl acetate;
Dimethyl sulfide;
Vanillin;
Methyl cinnamate;
Ethyl pelargonate;
Methyl anthranilate;
Isoamyl acetate;
Isobutyl acetate;
Alpha ionone;
Ethyl butyrate;
Acetic acid;
Gamma-undecalactone;
1-(3-(methylthio)butyryl-2,6,6-trimethyl cyclohexene;
1(3(methylthio)butyryl)-2,6,6-trimethyl-1,3-cyclohexadiene;
Naphthyl ethyl ether;
Diacetyl;
Ethyl acetate;
Anethole;
Isoamyl butyrate;
Cis-3-hexenol-1;
2-Methyl-2-pentenoic acid;
2-Methyl-cis-3-pentenoic acid;
Ethyl-2-methyl-cis-3-pentenoate;
Methyl-2-methyl-cis-3-pentenoate;
Elemecine (4-allyl-1,2,6-trimethoxy benzene);
Isoelemecine (4-propenyl-1,2,6-trimethoxy benzene); and
2-(4-hydroxy-4-methylpentyl)norbornadiene prepared according to U.S. Pat. No. 3,886,289, issued on May 27, 1975.

An additional aspect of our invention provides an organoleptically improved smoking tobacco product and additives therefor, as well as methods of making the same which overcome specific problems heretofore encountered in which specific desired sweet, spicy, vanilla-like, woody, hay, tobacco-like flavor and aroma characteristics are created or enhanced and may be readily controlled and maintained at the desired uniform level regardless of variations in the tobacco components of the blend.

This invention further provides improved tobacco additives and methods whereby various desirable sweet, spicy, vanilla-like, woody, hay, tobacco-like flavor and aroma characteristics may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient cyclic chemical compounds.

In addition to the cyclic chemical compounds of our invention, other flavoring and aroma additives may be added to the smoking tobacco material or substitute therefor either separately or in mixture with the cyclic chemical compounds as follows:

I. SYNTHETIC MATERIALS

Beta-ethyl-cinnamaldehyde;
Eugenol;
Dipentene;
β-Damascone;
β-Damascenone;
Maltol;

Ethyl maltol;
Delta undecalactone;
Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethyl naphtho-(2,1-b-)-furan;
4-Hydroxy hexanoic acid, gamma lactone;
Polyisoprenoid hydrocarbons defined in Example V of U.S. Pat. No. 3,589,372, issued on June 29, 1971

II. NATURAL OILS

Celery seed oil;
Coffee extract;
Bergamot Oil;
Cocoa extract;
Nutmeg oil; and
Origanum oil;

An aroma and flavoring concentrate containing one or more of the cyclic chemical compounds of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substituents (e.g., lettuce leaves) or mixtures thereof. The proportions of flavoring additives may be varied in accordance with taste but insofar as the augmentation, or the enhancement or the imparting of the sweet, spicy, vanilla-like, woody, hay, tobacco-like notes are concerned, we have found that satisfactory results are obtained if the proportion by weight of the sum total of cyclic chemical compounds to smoking tobacco material is between 250 ppm and 1,500 ppm (0.025%–1.5%) of the active ingredients to the smoking tobacco material. We have further found that satisfactory results are obtained if the proportion by weight of the sum total of cyclic chemical compounds used to flavoring material is between 2,500 and 10,000 ppm (0.25%–1.5%).

Any convenient method for incorporating the cyclic chemical compounds in the tobacco product may be employed. Thus, the cyclic chemical compounds taken alone or along with other flavoring additives may be dissolved in a suitable solvent such as ethanol, n-pentane, diethyl ether and/or other volatile organic solvents and the resulting solution may either be sprayed on the cured, cased and blended tobacco material or the tobacco material may be dipped into such solution. Under certain circumstances, a solution of the cyclic chemical compounds taken alone or taken further together with other flavoring additives as set forth above, may be applied by means of a suitable applicator such as a brush or roller on the paper or leaf wrapper for the smoking product, or it may be applied to the filter by either spraying to dipping or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the cyclic chemical compounds in excess of the amounts or concentrations above indicated so that when blended with other tobaccos, the final product will have the percentage within the indicated range.

In accordance with one specific example of our invention, an aged, cured and shredded plastic domestic burley tobacco is spread with a 20% ethyl alcohol solution of cyclic chemical compounds to provide a tobacco composition containing 800 ppm by weight of cyclic chemical compounds on a dry basis. Thereafter, the alcohol is removed by evaporation and the tobacco is manufactured into cigarettes by the usual techniques. The cigarette when treated as indicated has a desired and pleasing aroma which is detectable in the main and side streams when the cigarette is smoked. This aroma is described as being sweet, spicy, vanilla-like, woody, hay, and tobacco-like.

While our invention is particularly useful in the manufacture of smoking tobacco, such as cigarette tobacco, cigar tobacco and pipe tobacco, other tobacco products formed from sheeted tobacco dust or fines may also be used. Likewise, the cyclic chemical compounds of our invention can be incorporated with materials such as filter tip materials, seam paste, packaging materials and the like which are used along with tobacco to form a product adapted for smoking. Furthermore, the cyclic chemical compounds can be added to certain tobacco substitutes of natural or synthethic origin (e.g., dried lettuce leaves) and, accordingly, by the term "tobacco" as used throughout this specification is meant any composition intended for human consumption by smoking or otherwise, whether composed of tobacco plant parts or substitute materials or both.

One or more of the cyclic chemical compounds of our invention and one or more auxiliary perfume ingredients, including, for example, alcohols, aldehydes, nitriles, esters, ketones other than the cyclic chemical compounds of our invention, cyclic esters other than the cyclic chemical compounds of our invention, synthetic essential oils, ethers other than the cyclic chemical compounds of our invention, and natural essential oils may be admixed so that the combined odor of the individual components produce a pleasant and desired fragrance, particularly and preferably in floral fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute particular olfactory characteristics, but the over-all effect of the perfume composition will be the sum of the effects of each of the ingredients. Thus, the cyclic chemical compounds can be used to alter the aroma characteristics of a perfume composition, for example by utilizing or moderating the olfactory reaction contributed by another ingredient in the composition.

The amount of cyclic chemical compounds of our invention which will be effective in perfume compositions depends on many factors, including the other ingredients, their amounts and the effects which are desired. It has been found that perfume compositions containing as little as 0.1% of cyclic chemical compounds (e.g., 0.05%) can be used to impart sweet, fruity and green aroma nuances to soaps, cosmetics or other products. The amount employed can range up to 10% of the fragrance components and will depend on considerations of cost, nature of the end product, the effect desired on the finished product and the particular fragrance sought.

The cyclic chemical compounds of our invention are useful, taken alone or in perfume compositions as olfactory components in detergents and soaps, space odorants and deodorants, perfumes, colognes, toilet water, bath preparations, such as bath oils, and bath solids; hair preparation, such as lacquers, brilliantines, pomades and shampoos; cosmetic preparations, such as creams, deodorants, hand lotions and sun screens; powders, such as talcs, dusting powders, face powders and the like. When used as an olfactory component, as little as 0.1% of the cyclic chemical compounds will suffice to impart a sweet, fruity and green aroma nuance to fragrance formulations. Generally, no more than 3% of cyclic chemical compounds of our invention based on the ultimate end product is required in the perfume composition.

Insofar as perfumed articles are concerned the amount of cyclic chemical compound of our invention having the structure:

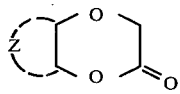

wherein Z is benzo or cyclohexano can vary from 0.01% by weight up to 3.0% by weight based on the total weight of the perfumed article, that is based on the total weight of anionic, cationic or nonionic solid or liquid detergent base; or fabric softener composition; or fabric softener article.

In addition, the perfume composition or fragrance composition of our invention can contain a vehicle, or carrier for the cyclic chemical compounds of our invention. The vehicle can be a liquid such as a non-toxic alcohol, a non-toxic glycol, or the like. The carrier can also be an absorbent solid, such as a gum (e.g., gum arabic) or components for encapsulating the composition (such as gelatin).

It will thus be apparent that cylic chemical compounds can be utilized to alter the sensory properties, particularly organoleptic properties, such as flavors and/or fragrances of a wide variety of consumable materials.

The following examples are illustrative and the invention is to be considered to be restricted thereto only as indicated in the appended claims. These examples serve to illustrate processes for producing the cyclic chemical compounds useful in our invention and processes for using the cyclic chemical compounds of our invention for their organoleptic properties.

All parts and percentages given are by weight unless otherwise specified.

EXAMPLE I: PREPARATION OF 1,4-BENZODIOXAN-2-ONE

Reaction:

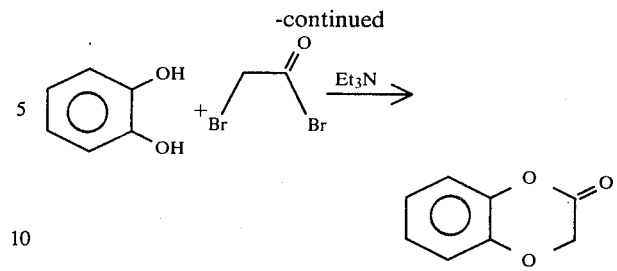

Triethylamine (200 grams, 2 moles) is added dropwise to a solution of 120 grams (1 mole) of catechol in 500 ml of toluene at 50° C. Bromoacetyl bromide (1 mole) is added over a one hour period with stirring and the reaction mass is heated to reflux. After one hour, the mass is cooled and 500 mls of water are added thereto. The organic layer is washed twice with 25 ml of water. The toluene is removed under reduced pressure to afford 135 grams of a crude solid. Recrystallization from ethanol affords 105 grams of colorless needles (m.p. 53°–55° C.) which is identified as 1,4-benzodioxan-2-one.

Figure 1:
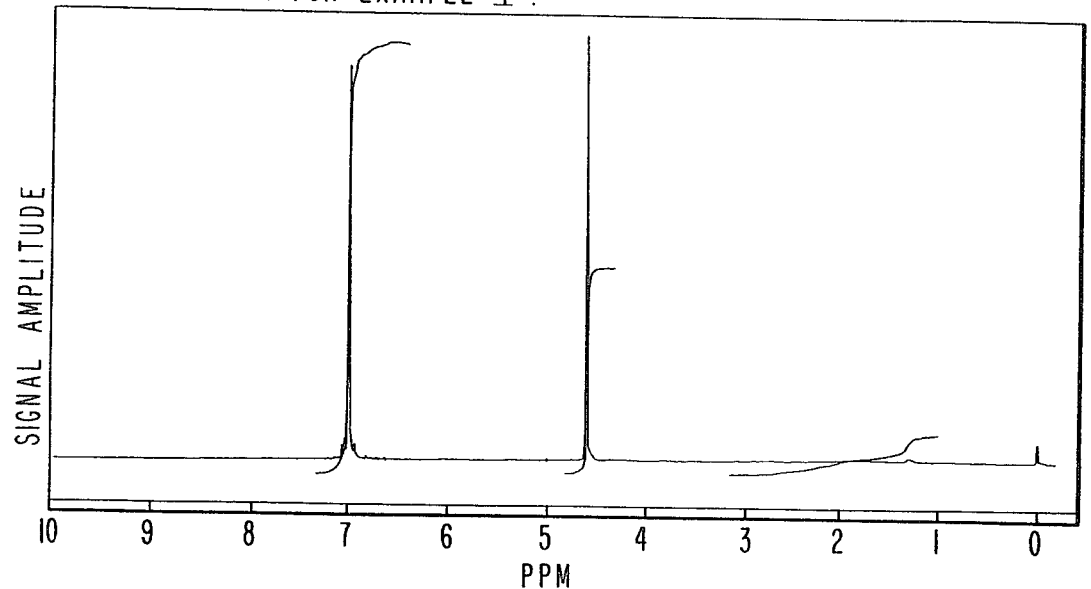
FIG. 1 is the NMR spectrum for the compound produced according to Example I having the structure.

FIG. 1 shows the NMR spectrum of 1,4-benzodioxan-2-one.

FIG. 2 shows the IR spectrum of 1,4-benzodioxan-2-one.

EXAMPLE II: PREPARATION OF 1,4-BENZODIOXAN-2-ONE

Reaction:

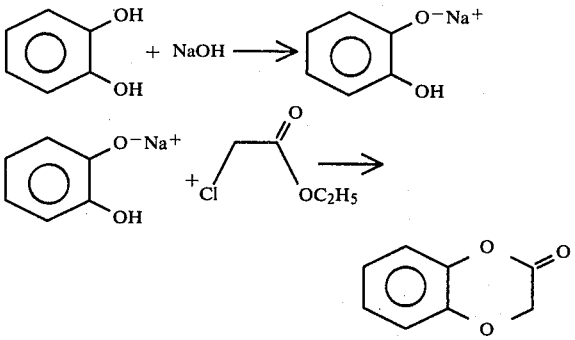

To a stirred solution of 120 grams of catechol and 10 grams of Aliquat ® 336 (brand of tricaprylmethylammonium chloride, of General Mills Chemical Company of Minneapolis, Minnesota) at 80° C. is added ethyl chloroacetate (87 grams, 1 mole) over a one hour period. The reaction mass is stirred for one hour and then cooled. 1000 ml of dilute (5%) hydrochloric acid is added with stirring. The aqueous layer is discarded. The organic layer is washed twice with a minimum amount of water. The toluene is distilled off under reduced pressure to afford 119 grams of crude product. Recrystallization from ethanol afforded 92 grams of 1,4-benzodioxan-2-one.

EXAMPLE III: PREPARATION OF TRANS-HEXAHYDRO-1,4-BENZODIOXAN-2-ONE

Reaction:

-continued

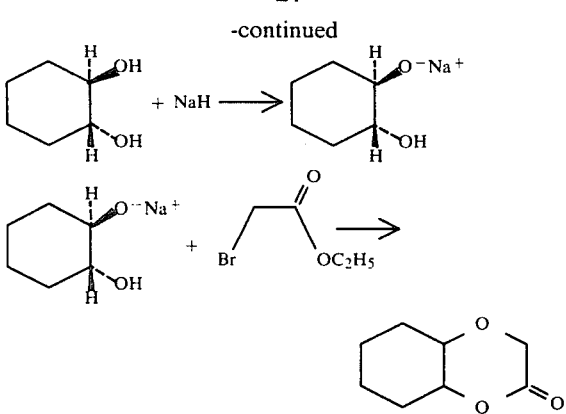

To a slurry of 54 grams of 55% sodium hydride in 1000 mls of toluene is portionwise added 140 grams of trans-1,2-cyclohexanediol at 90° C. with concommitant release of hydrogen. The resulting mass, containing the monosodium salt of trans-1,2-cyclohexanediol is stirred at 100° C. for 30 minutes. Ethyl bromoacetate (203 grams) is added dropwise to the stirred reaction mass at 100° C. over a 30 minute period. After stirring for 30 minutes, the mass is cooled to 20° C. Water (100 ml) is added and the organic layer is distilled to afford 130 grams of trans-hexahydro-1,4-benzodioxan-2-one. The product is purified by distillation through a 1"×12" Goodloe ®  packed column to afford a semi solid (m.p. 20°–22° C., bp. 97° C. at 1.2 mm).

FIG. 3 is the NMR spectrum of fraction 4.
FIG. 4 is the IR spectrum of fraction 4.

EXAMPLE IV: PERFUME COMPOSITION

The following mixture is prepared:

| Ingredient | Grams |
| --- | --- |
| Benzyl acetate | 50 |
| Rosewood Oil | 100 |
| Cedarwood Oil | 150 |
| Linalyl acetate | 100 |
| α-Ionone | 80 |
| Ethyl cinnamate | 20 |
| Amyl cinnamic aldehyde | 50 |
| Iso-eugenol | 50 |
| Compound produced according to Example I having the structure: 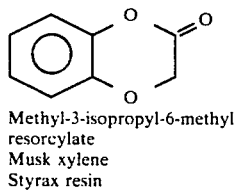 | 100 |
| Methyl-3-isopropyl-6-methyl resorcylate | 50 |
| Musk xylene | 50 |
| Styrax resin | 100 |

The foregoing perfume formulation is an important part of chypre essence. The coumarin ordinarily used in this formulation has been replaced by the compound having the structure:

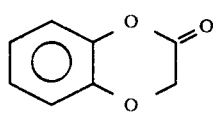

produced according to Example I or Example II. The methyl-3-isopropyl-6-methyl-resorcylate is used as a replacement for the oakmoss. This perfume is incorporated into a soap at the 0.1% level. A natural and distinctly oakmoss note is given to the soap.

EXAMPLE V: PERFUME COMPOSITION

The following mixture is prepared:

| Ingredient | Grams |
| --- | --- |
| Benzyl acetate | 50 |
| Rosewood Oil | 100 |
| Cedarwood Oil | 150 |
| Linalyl acetate | 100 |
| α-Ionone | 80 |
| Ethyl cinnamate | 20 |
| Amyl cinnamic aldehyde | 50 |
| Iso-eugenol | 50 |
| Compound produced according to Example III having the structure: 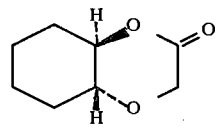 | 100 |
| Methyl-3-n-butyl-6-methyl resorcylate | 200 |
| Musk xylene | 50 |
| Styrax resin | 100 |

The foregoing perfume formulation is an important part of chypre essence. The coumarin ordinarily in this formulation has been replaced by the compound produced according to Example III having the structure:

The methyl-3-n-butyl-6-methyl resorcylate is used as a replacement for oakmoss. This perfume is incorporated into a soap at the 0.1% level where a natural oakmoss aroma is imparted to said soap.

EXAMPLE VI: BASIC WALNUT FORMULATION

The following basic walnut formulation is prepared:

| Ingredients | Parts by Weight |
| --- | --- |
| Cyclotene | 4 |
| Vanillin | 1 |
| Butylisovalerate | 2 |
| Benzaldehyde | 6 |
| 2,3-Diethyl pyrazine (10% in ethyl alcohol) | 2 |
| Ethyl-2-methyl valerate | 2 |
| gamma-Butyrolactone | 20 |
| gamma-Hexenolactone | 10 |
| 2,4-Decadienal (0.1% in ethyl alcohol) | 0.5 |
| 2,4-Heptadienal (0.1% in ethyl alcohol) | 0.5 |
| Butylidene phthalide | 2 |
| Propylene glycol USP | 95 |

The basic walnut formulation is divided into two parts. To the first part 0.5% by weight of the compound prepared according to Example I having the structure:

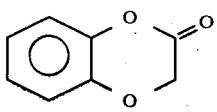

is added. Both flavors with and without the additional material are compared at the rate of 100 parts per million in water by a bench panel consisting of four people. The walnut flavor with the addition of the compound prepared according to Example I having the structure:

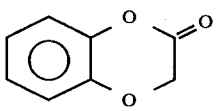

is considered to have characteristic fatty/oily walnut notes both in aroma and taste, with an additional astringent taste and bitter notes which increase the mouthfeel of the flavor; whereas the flavor without the compound prepared according to Example I lacks the characteristic walnut flavor.

EXAMPLE VII: BASIC WALNUT FORMULATION

The following basic walnut formulation is prepared:

| Ingredients | Parts by Weight |
| --- | --- |
| Cyclotene | 4 |
| Vanillin | 1 |
| Butylisovalerate | 2 |
| Benzaldehyde | 6 |
| 2,3-Diethyl pyrazine (10% in ethyl alcohol) | 2 |
| Ethyl-2-methyl valerate | 2 |
| gamma-Butyrolactone | 20 |
| gamma-Hexenolactone | 10 |
| 2,4-Decadienal (0.1% in ethyl alcohol) | 0.5 |
| 2,4-Heptadienal (0.1% in ethyl alcohol) | 0.5 |
| Butylidene phthalide | 2 |
| Propylene glycol USP | 95 |

The formulation is divided into two parts. To one of the parts 0.5% by weight of the compound having the structure:

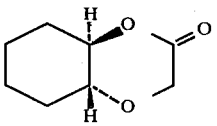

prepared according to Example III is added. To the second part of the basic walnut formulation nothing else is added. Both formulations, with and without, the additional material are compared at the rate of 100 ppm in water by a bench panel. All members of the bench panel prefer the walnut flavor with the addition of the compound prepared according to Example III having the structure:

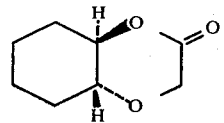

the characteristic oily, walnut notes and bitter mouthfeel effect are present.

EXAMPLE VIII: PERFUME FORMULATION

The following Fougère perfume formulation is prepared:

| Ingrediens | Parts by Weight | |
| --- | --- | --- |
| Oakmoss Absolute (50% in DEP) | 2 | 2 |
| Bergamot Oil | 15 | 15 |
| Lavender Oil | 19 | 19 |
| Citronellol | 15 | 15 |
| Patchouli Oil | 4 | 4 |
| Geranium Oil | 5 | 5 |
| gamma Methyl Ionone | 15 | 15 |
| Petitgrain Oil | 2 | 2 |
| Musk Ketone | 8 | 8 |
| Heliotropine | 2 | 2 |
| Clary Sage Oil | 2 | 2 |
| Amyl Salicylate | 1 | 1 |
| 1,4-Benzodioxan-2-one (produced according to Example I) having the structure | 10 | — |

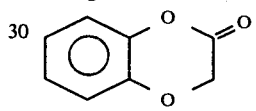

The compound of Example I gives surprising strength to this Fougère formulation and in addition acts as a fixative therefor. Addition of the compound produced according to Example I greatly increases the aesthetic qualities and gives the olfactory sensation of sweet, coumarin-like notes.

EXAMPLE IX: TOBACCO FORMULATION

A tobacco mixture is produced by admixing the following ingredients:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredients | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above stated tobacco flavor formulation is applied at the rate of 0.1% to all of the cigarettes produced using the above tobacco formulation. Half of the cigarettes are then treated with 500 or 1000 ppm of the compound produced according to Example III having the structure:

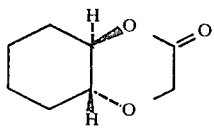

The control cigarettes not containing the compound produced according to Example III and the experimental cigarettes which contain the compound produced according to Example III are evaluated by paired comparison and the results are as follows:

The experimental cigarettes are found to have more body and to be on smoking more tobacco like, more aromatic, sweet, spicy, hay, tobacco-like.

The tobacco of the experimental cigarettes prior to smoking has a sweet, spicy, vanilla-like, woody, hay, tobacco-like aroma.

The product of Example III produced according to the process of Example III enhances the tobacco-like taste and aroma of the blended cigarette imparting to it woody, vanilla-like tobacco notes.

EXAMPLE X: PERFUMED LIQUID DETERGENT

Concentrated liquid detergents with sweet, fruity, green, coumarin-like aroma nuances are prepared containing 0.10%, 0.15%, and 0.20% of the compound produced according to Example III having the structure:

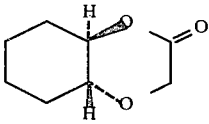

They are prepared by adding and homogeneously mixing the appropriate quantity of hexahydro(trans)-1,4-benzodioxan-2-one prepared according to Example III in the liquid detergent. The detergents all possess a sweet, fruity, green, coumarin-like fragrance. The intensity increasing with greater concentrations of hexahydro(trans)-1,4-benzodioxan-2-one.

EXAMPLE XI: PREPARATION OF COLOGNE AND HANDKERCHIEF PERFUME

Hexahydro(trans)-1,4-benzodioxan-2-one, prepared according to the process of Example III, is incorporated into cologne at concentrations of 1.5%, 2.0%, 2.5%, 3.0%, 3.5% and 4.0% in 80%, 85% and 90% aqueous ethanol; and into hankerchief perfumes at concentrations of 10%, 15%, 20% and 25% (in 80%, 85%, 90% and 95% aqueous ethanol composition). In each of the compositions tested distinctive and definite sweet, fruity, green, coumarin-like aroma nuances are imparted to the colognes and to the handkerchief perfumes.

EXAMPLE XII: PREPARATION OF COLOGNE AND HANDKERCHIEF PERFUME

The composition of Example IV is incorporated into colognes at concentrations of 1.5%, 2.0%, 2.5%, 3.0%, 3.5% and 4.0% in 80%, 85% and 90% aqueous ethanol; and into handkerchief perfumes at concentrations of 15%, 20%, 25% and 30% (in 80%, 85%, 90% and 95% aqueous ethanol). The use of the composition of Example IV affords a distinct and definite strong chypre aroma to the handkerchief perfume and cologne in each case.

EXAMPLE XIII: PREPARATION OF A SOAP COMPOSITION

100 Grams of soap chips are mixed with 1 gram of 1,4-benzodioxan-2-one produced according to the process of Example II until a substantially homogeneous composition is obtained. The perfumed soap composition manifests an excellent green, coumarin-like aroma.

EXAMPLE XIV: PREPARATION OF A DETERGENT COMPOSITION

A total of 100 grams of detergent phosphate powder is mixed with 0.15 grams of 1,4-benzodioxan-2-one produced according to Example II until a substantially homogeneous composition is obtained. The composition has an excellent green, coumarin-like aroma.

EXAMPLE XV

A. Powder Flavor Composition

20 Grams of the flavor composition of Example VI is emulsified in a solution containing 300 grams gum acacia and 700 grams of water. The emulsion is spray dried with a Bowen Lab Model Dryer utilizing 260 c.f.m. of air with an inlet temperature of 500° F. and an outlet temperature of 200° F., and a wheel speed of 50,000 rpm.

B. Sustained Release Flavor

The following mixture is prepared:

| Ingredient | Parts By Weight |
|---|---|
| Liquid Walnut Flavor composition of Example VI (containing 1,4-benzodioxan-2-one) | 20 |
| Propylene Glycol | 9 |
| Cab-O-sil ® M-5 (Brand of Silica produced by the Cabot Corp. of 125 High St., Boston, Mass. 02110; Physical Properties: Surface Area: 200 m²/gm Nominal particle size: 0.012 microns; Density: 2.3 lbs/cu.ft.) | 5.00 |

The Cab-O-Sil ® is dispersed in the liquid walnut flavor composition of Example VI with vigorous stirring thereby resulting in a viscous liquid. 71 Parts by weight of the powder flavor composition of Part A supra is then blended into said viscous liquid with stirring at 25° C. for a period of 30 minutes resulting in a dry, free flowing sustained release flavor powder.

EXAMPLE XVI

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example VI is added to the solution which is then homogenized to form an emulsion having a particle size typically in the range of 2–5 microns. The material is kept at 120° F. under which conditions the gelatin will not gel.

Coacervation is induced by adding, slowly and uniformly 40 parts by weight of a 20% aqueous solution of sodium sulphate. During coacervation the gelatin molecules are deposited uniformly about each oil droplet as a nucleus.

Gelation is effected by pouring the heated coacervate mixture into 1000 parts by weight of a 7% aqueous solution of sodium sulphate at 65° F. The resulting gelled coacervate may be filtered and washed with water at temperatures below the melting point of gelatin, to remove the salt.

Hardening of the filter cake, in this example, is effected by washing with 200 parts by weight of 37% solution of formaldehyde in water. The cake is then washed to remove the residual formaldehyde.

EXAMPLE XVII: CHEWING GUM

100 Parts by weight of chicle are mixed with 4 parts by weight of the flavor prepared in accordance with Example XV. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting sweet, fruity, walnut flavor.

EXAMPLE XVIII: CHEWING GUM

100 Parts by weight of chicle are mixed with 18 parts by weight of the flavor prepared in accordance with Example XVI. 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing the chewing gum has a pleasant long lasting sweet, fruity, walnut flavor.

EXAMPLE XIX: TOOTHPASTE FORMULATION

The following separate groups of ingredients are prepared:

| Parts by Weight | Ingredients |
| --- | --- |
| Group "A" | |
| 30.200 | Glycerin |
| 15.325 | Distilled Water |
| .100 | Sodium Benzoate |
| .125 | Saccharin Sodium |
| .400 | Stannous Flouride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example XV |
| 100.00 (Total) | |

PROCEDURE

1. The ingredients in Group "A" are stirred and heated in a steam jacketed kettle to 160° F.

2. Stirring is continued for an additional three to five minutes to form a homogeneous gel.

3. The powders of Group "B" are added to the gel, while mixing until a homogenous paste is formed.

4. With stirring, the flavor of "D" is added and lastly the sodium n-lauroyl sacrosinate.

5. The resultant slurry is then blended for one hour. The completed paste is then transferred to a three roller mill and then homogenized, and finally tubed.

The resulting toothpaste when used in a normal tooth-brushing procedure yields a pleasant sweet, walnut flavor, of constant strong intensity throughout said procedure (1–1.5 minutes).

EXAMPLE XX: CHEWABLE VITAMIN TABLES

The flavor material produced according to the process of Example XVI is added to a Chewable Vitamin Tablet Formulation at a rate of 10 gm/Kg which Chewable Vitamin Tablet Formulation is prepared as follows:

In a Hobart Mixer, the following materials are blended to homogeneity:

| Ingredients | Gms/1000 Tablets |
| --- | --- |
| Vitamin C (ascorbic acid as ascorbic acid-sodium ascorbate mixture 1:1 | 70.0 |
| Vitamin $B_1$ (thiamine mononitrate) as Rocoat ® thiamine monomitrate 33⅓% (Hoffman La Roche) | 4.0 |
| Vitamin $B_2$ (riboflavin) as Rocoat ® riboflavin 33⅓% | 5.0 |
| Vitamin $B_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin $B_{12}$ (cyanocobalamin) as Merck 0.1% in gelatin | 3.5 |
| Vitamine E (dl-alpha tocopheryl acetate) as dry Vitamin E acetate 33⅓% Roche | 6.6 |
| d-Biotin | 0.044 |
| Certified lake color | 5.0 |
| Flavor of Example XVI | (as indicated above) |
| Sweetener sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong sweet, walnut flavor for a period of 12 minutes.

EXAMPLE XXI: CHEWING TOBACCO

Onto 100 pounds of tobacco for chewing (85% Wisconsin leaf and 15% Pennsylvania leaf) the following casing is sprayed at a rate of 30%:

| Ingredients | Parts by Weight |
| --- | --- |
| Corn Syrup | 60 |
| Licorice | 10 |
| Glycerine | 20 |
| Fig Juice | 4.6 |
| Pruce Juice | 5 |

|Ingredients|Parts by Weight|
|---|---|
|Flavor Material of Example XV|0.4|

The resultant product is redried to a moisture content of 20%. On chewing, this tobacco has an excellent substantially consistent, long-lasting sweet, green, walnut (20 minutes) nuance in conjunction with the main fruity tobacco note.

EXAMPLE XXII: PREPARATION OF A SOLID DETERGENT COMPOSITION

A detergent is prepared from the following ingredients according to Example I of Canadian Pat. No. 1,007,948:

| |Percent by Weight|
|---|---|
|"Neodol 45-11" (a $C_{14}$-$C_{15}$ alcohol ethoxylated with 11 moles of ethylene oxide)|12|
|Sodium carbonate|55|
|Sodium citrate|20|
|Sodium sulfate, water brighteners|q.s.|

This detergent is a "phosphate-free" detergent. A total of 100 grams of this detergent is admixed with 0.15 grams of the chypre base perfume of Example IV. The detergent has an excellent green, chypre aroma.

EXAMPLE XXIII: PERFUMED LIQUID DETERGENT

Concentrated liquid detergents (Lysine salt of n-dodecylbenzene sulfonic acid as more specifically described in U.S. Pat. No. 3,948,818, issued on Apr. 6, 1976) with green, chypre aromas are parpared containing 0.50% of the perfume formulation of Example IV. They are prepared by adding and homogeneously mixing the appropriate quantity of perfume formulation in the liquid detergent. The detergents all possess green, chypre aroma nuances, the intensity of each of the foregoing characteristics increasing with greater concentrations of perfume formulations in the detergent.

EXAMPLE XXIV

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:

1. a water "dissolvable" paper ("Dissolvo Paper").
2. Adogen 448 (m.p. about 140° F.) as the substrate coating; and
3. An outer coating having the following formulation (m.p. about 150° F.):
   57 percent $C_{20\text{-}22}$ HAPS
   22 percent isopropyl alcohol
   20 percent antistatic agent
   1 percent of the bicyclic compound prepared according to Example III having the structure:

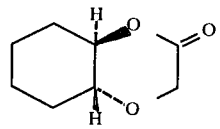

The compound having the structure:

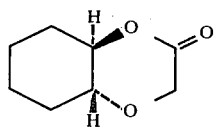

prepared according to Example III gives rise to an excellent sweet, green, coumarin-like aroma.

A fabric softening composition prepared as set forth above having the above aroma characteristics essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The aroma as set forth above is imparted in a pleasant manner to the head space in the dryer on operation thereof using the said dryer added fabric softening nonwoven fabric.

What is claimed is:

1. A fabric softener article comprising a substrate and a coating therefor and in intimate contact with said coating an aroma augmenting or enhancing quantity of at least one cyclic chemical compound having the structure:

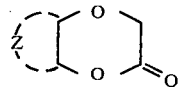

wherein Z represents benzo or cyclohexano.

2. A process for augmenting or enhancing the aroma of a fabric softener or article or a fabric softener composition comprising the step of intimately admixing with said fabric softener composition or with the coating composition for said fabric softener article at least one cyclic chemical compound having the structure:

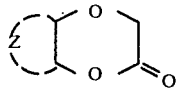

wherein Z represents benzo or cyclohexano in an aroma augmenting or enhancing concentration.

* * * * *